United States Patent
Beck et al.

[11] Patent Number: 5,147,385
[45] Date of Patent: Sep. 15, 1992

[54] STENT AND CATHETER FOR THE INTRODUCTION OF THE STENT

[75] Inventors: Andreas Beck, Hornberg; Norbert A. Nanko, Freiburg, both of Fed. Rep. of Germany

[73] Assignee: Schneider (Europe) A.G., Zurich, Switzerland

[21] Appl. No.: 603,576

[22] Filed: Oct. 25, 1990

[30] Foreign Application Priority Data

Nov. 1, 1989 [CH] Switzerland ............. 03946/89

[51] Int. Cl.⁵ ............. A61F 2/06; A61F 7/12
[52] U.S. Cl. ............. 623/1; 623/12; 128/401; 606/194
[58] Field of Search ............. 604/96–98, 604/103–109, 265, 266; 606/27–33, 7, 41, 195, 194, 198; 128/399–401; 623/11, 12, 1

[56] References Cited

U.S. PATENT DOCUMENTS

| | | | |
|---|---|---|---|
| 4,286,341 | 9/1981 | Greer et al. | 623/1 |
| 4,739,762 | 4/1988 | Palmaz | 604/104 |
| 4,740,207 | 4/1988 | Kreamer | 623/12 |
| 4,763,653 | 8/1988 | Rockey | 604/194 |
| 4,795,458 | 1/1989 | Regan | 623/12 |
| 4,799,479 | 1/1989 | Spears | 606/7 |
| 4,870,966 | 10/1989 | Dellon et al. | 623/1 |
| 4,877,030 | 10/1989 | Beck et al. | 606/195 |
| 4,923,464 | 5/1990 | Di Pisa, Jr. | 606/195 |
| 4,923,470 | 5/1990 | Dumican | 623/1 |
| 4,955,377 | 9/1990 | Lennok et al. | 128/401 |

FOREIGN PATENT DOCUMENTS

| | | | |
|---|---|---|---|
| 0194192 | 9/1986 | European Pat. Off. | 623/12 |
| 0202444 | 11/1986 | European Pat. Off. | 623/12 |
| 2222954 | 3/1990 | United Kingdom | 623/12 |

*Primary Examiner*—C. Fred Rosenbaum
*Assistant Examiner*—Sharon Finkel
*Attorney, Agent, or Firm*—Peter C. Richardson; Lawrence C. Akers; Thomas C. Naber

[57] ABSTRACT

A method for using stent which is a hollow, cylindrical structure made of a synthetic substance which becomes plastic and malleable in a temperature range from 45° to 75° Celsius. The stent is brought to the desired site, for example a stenosed section of an artery, by means of a heatable balloon catheter. The stent is heated at the site to be treated and whilst in the plastic state is expanded through dilatation of a balloon. After being cooled to body temperature the expanded stent retains the form achieved. The body fluids bring about complete biodegradation of the implanted stent.

5 Claims, 1 Drawing Sheet

STENT AND CATHETER FOR THE INTRODUCTION OF THE STENT

BACKGROUND OF THE INVENTION

This discovery concerns a stent as per the general description given in the independent Patent Claim 1 and also a balloon catheter for the introduction of the stent. Stents and more specifically intravascular stents for angioplasty have largely proved useful in medical practice for the prevention of occlusions or re-stenosis after transluminal angioplasty. A known stent consists of a cartridge-shaped lattice made of stainless steel. The stent, which measures 1.6 or 3 mm in circumferences, is attached to a folded balloon catheter and is brought to the desired site of the blood vessel percutaneously. The stent is widened to a diameter of about 3 mm by dilating the balloon catheter. The inserted and fixed stent is left in the vessel and as a rule becomes covered with newly formed intima. The article by Julio C. Palmaz in the journal *Radiology*, July 1988, 150: 1263-1269 deals with the state of the art in respect of this technique.

SUMMARY OF THE INVENTION

The objective behind the discovery was to produce a stent of the kind described which would be even more safe and simple to use but which nevertheless could be manufactured at a lower cost. This objective has been achieved through the discovery as described under Claim 1.

The discovered stent is pushed on to the balloon of the balloon catheter at room temperature and is comparatively rigid and stiff here. The stent can be fixed on to the catheter by slightly dilating the balloon. Once the stent has been pushed forwards to the desired site, for example in a stenosed section of an artery, it is heated through a heating facility arranged in the catheter, until it can be widened radially through dilatation of the balloon. The stent is widened until it sits closely up against the inner wall of the vessel with slight pressure. The heating of the catheter is now stopped, whereupon the stent changes into the solid state comparatively rapidly and retains the dilated form here. In the implanted state the wall-thickness of the stent is less than in its original state so that it is somewhat more flexible. The stent can therefore adapt to the course of the vessel, within certain limits, in the implanted state. The discovered stent can be made of a synthetic substance which is presumably better tolerated than metal. Here the inside of the stent can be completely smooth, which reduces the danger of thrombosis.

The discovered stent is particularly suitable for coronary and peripheral angioplasty, but other applications are also conceivable. For example, the discovered stent would be suitable for use whenever it is a question of keeping a passageway permanently or temporarily open. Examples of such passageways are the cystic duct and the urethra.

The stent can be manufactured, for example through extrusion, in a great variety of lengths and also external and internal diameters. A stent of the most suitable dimensions can thus be supplied in every case. A stent with smaller external - and internal - diameters is chosen for the treatment of a coronary artery for example, than for the treatment of a peripheral artery. Similarly, a comparatively short stent is generally used for the treatment of a curved section of vessel.

Following further development of the discovery, the stent is made of a material which is completely biodegradable in body fluids. Aliphatic polyester materials are particularly suitable for this and more specifically materials made of poly (e-caprolactone). The biological degradation of these synthetic substances is known. Such substances are already used in medicine for the fixation of prostheses and as capsules for the controlled delivery of drugs. The rate of degradation of the material used to manufacture the discovered stent is roughly such that it is completely or largely dissolved within about 2 to 6 months. Since the stent is no longer present at the treated site after a comparatively short period of time, in the case of treatment for a stenosis the risk of thrombosis is less than with a permanently indwelling stent.

BRIEF DESCRIPTION OF THE DRAWINGS

A model specimen of the discovery is explained in more detail on the basis of the following drawings.

DETAILED DESCRIPTION OF A PREFERRED EMBODIMENT

Figure 1:
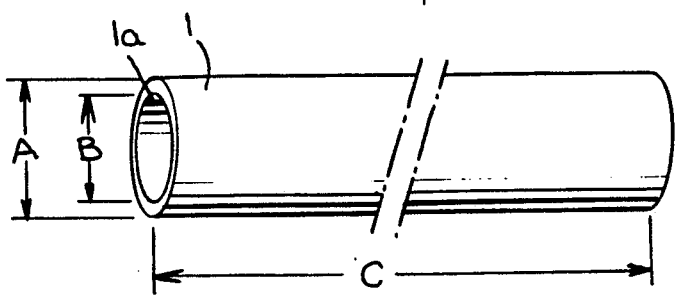
FIG. 1 shows a perspective view of a stent, as per the discovery.

The stent shown in FIG. 1 is a hollow cylindrical structure with a length C of, for example, 2 to 10 cm. For the treatment of a coronary artery the internal diameter B would be 1.0 0.005 mm for example, and the external diameter A 1.6 mm. For the treatment of a peripheral artery the internal diameter B would be 2.0 mm for example, and the external diameter A 3.0 mm. The stent 1 can be manufactured by extrusion. A synthetic substance which melts or which changes into the plastic state through gradual softening in the temperature range from 45° to 75° Celsius is suitable as the manufacturing material. Aliphatic polyesters and in particular poly (E-caprolactone) are a suitable material. Also suitable are polymers which are solid below a temperature of 45° Celsius and which change into a non-crystalline state at least above a temperature of about 70° Celsius. Suitable polymers are polycaprolactones, polyurethanes and polyamides.

Out of these polymers, those which are biodegradable in body fluids are particularly suitable. Poly (E-caprolactone) is particularly suitable here, the in vivo degradation of which has been described in the Journal of Applied Polymer Sciences, Vol. 26, 3779-3787 (1981).

A heatable balloon catheter 3 is used in order to bring the stent 1 to the desired treatment site. This catheter has a shaft 2, with three lumina, one lumen 2a being used for the passage of a guidewire.

A salt solution circulates in the other two lumina 2b and 2c, this flowing into and out of the internal space of the balloon 3 through openings which are not shown here. The salt solution is heated and conveyed by a heating - and pump - facility arranged at the proximal end of the shaft 2. Balloon catheters which are heated in the usual known way electrically, with high frequency or micro-waves, could also be used here however.

Figure 2A:
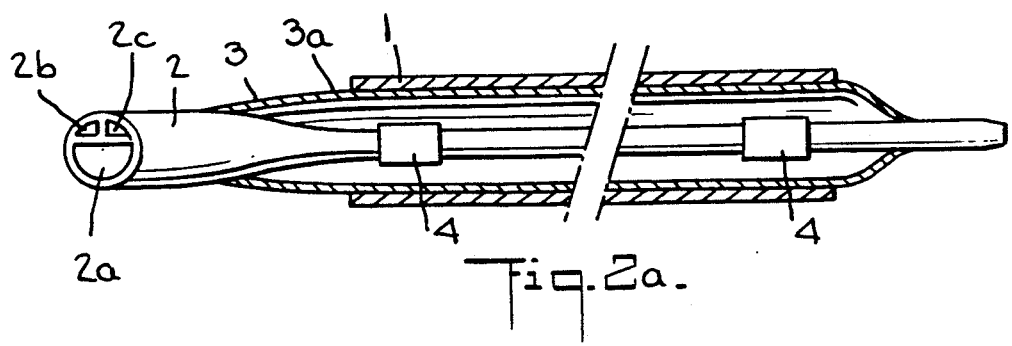
FIGS. 2a and 2b show the front end of a balloon catheter with a stent, as per the discovery, before and after dilatation.

In order to fix the stent 1 on to the balloon catheter it is pushed on to the folded balloon from the distal end. In many cases the stent 1 is fixed sufficiently to prevent displacement in a longitudinal direction through the fact that its inside 1a rubs against the outside 3a of the balloon 3. In other cases the pressure is increased slightly in the balloon 3. As shown in FIG. 2a, the length of the balloon 3 is selected in such a way that this is somewhat longer than the length C of the stent 1. The entire internal surface 1a of the stent 1 thus lies up against the external surface 3a of the balloon. When the balloon catheter is not yet heated the stent 1 is comparatively rigid and stiff and is not expanded, even when there is comparatively high pressure in the balloon 3.

The catheter, with the stent 1 placed on it, is introduced in the usual known way. For the treatment of a stenosis the catheter is introduced percutaneously with the aid of a guidewire, which is not shown here. The position of the stent 1 can be monitored radiographically, for example using know marking strips 4.

Figure 2B:
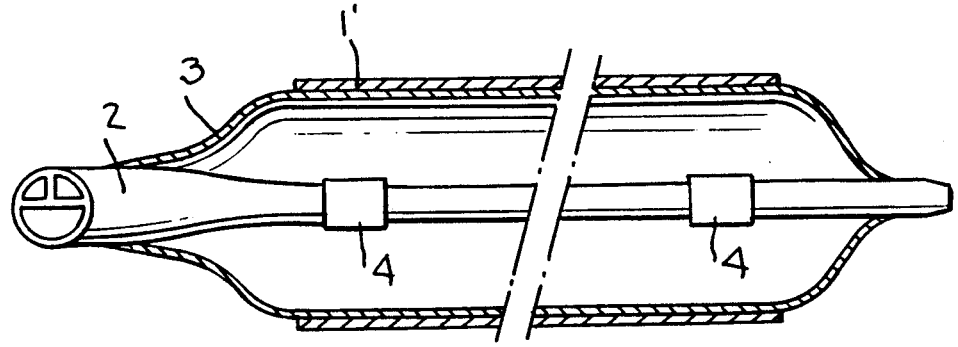

Once the stent 1 has been brought to the desired site with the balloon catheter, the balloon 3 is heated and the stent 1 is brought to a temperature at which plastic expansion becomes possible through dilatation of the balloon 3. For the treatment of a coronary artery, for example, the internal diameter is increased to 2.7 mm and the external diameter to 3.0 mm. In the case of a peripheral artery the internal diameter of the dilated stent is 5.4 mm for example, and the external diameter is 6.0 mm. The wall-thickness of the dilated stent 1' is considerably smaller than that of the original stent 1, as may be seen from FIGS. 2a and 2b.

Figure 3A:
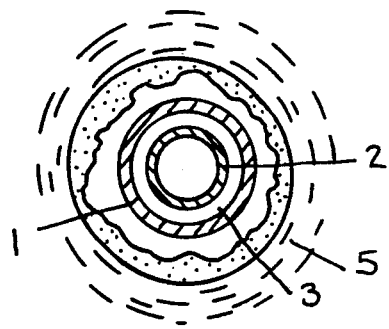
FIGS. 3a and 3b show diagrammatically a section through a vessel with the stent inserted before and after dilatation.
Figure 3B:
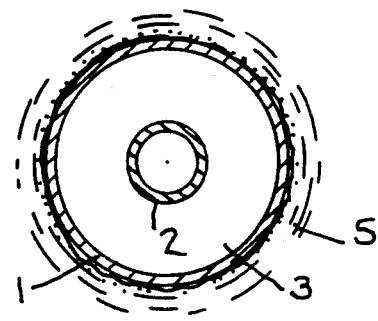

The stent 1 is dilated until its outer surface lies up against the inside of the vessel with slight pressure. This is shown in diagram form in FIGS. 3a and 3b. In this case the vessel 5, for example, is a stenosed section of artery 5.

Once the stent 1' is fixed in the vessel the heating of the catheter is stopped, and the temperature of the stent 1' then falls to body temperature, once again assuming the solid state here. The pressure in the balloon 3 is then reduced and the catheter is removed from the vessel in the usual known way.

If the stent 1' is made of poly (E-caprolactone), then auto-catalytic degradation takes place through hydrolytic outer cleavage and it is broken down completely in about 2 to 6 months.

We claim:

1. A method of treating a stenosed section of a blood vessel; said method comprising:
    a) providing an intravascular stent having a hollow cylindrical structure and constructed of a material which has a melting point or a softening range between about 45° and 75° Celsius;
    b) providing a balloon catheter having means whereby the balloon thereof is heatable when disposed intravascularly;
    c) mounting the stent on said balloon by slightly inflating the balloon;
    d) employing the balloon catheter to deliver the mounted stent to the stenosed section;
    e) heating the balloon to a temperature sufficient to soften the stent mounted thereon, and subsequently inflating the balloon to thereby radially expand the stent until it resides against the inner wall of the vessel with slight pressure;
    f) discontinuing the heating of the balloon to thereby allow the stent to harden in its radially expanded configuration; and
    g) deflating the balloon and withdrawing the balloon catheter.

2. A method as claimed in claim 1 wherein the stent material is biodegradable in body fluids.

3. A method as claimed in claim 2 wherein the material is a polymer.

4. A method as claimed in claim 3 wherein the material is an aliphatic polyester.

5. A method as claimed in claim 4 wherein the material is poly-E-caprolactone.

* * * * *